US00PP15747P2

(12) United States Plant Patent
Miller

(10) Patent No.: US PP15,747 P2
(45) Date of Patent: May 3, 2005

(54) ***BRUGMANSIA* PLANT NAMED 'MINER'S CLAIM'**

(50) Latin Name: *Brugmansia×hybrida*
Varietal Denomination: Miner's Claim

(76) Inventor: Luen Miller, 316 Berkeley Way, Santa Cruz, CA (US) 95062

( * ) Notice: Subject to any disclaimer, the term of this patent is extended or adjusted under 35 U.S.C. 154(b) by 5 days.

(21) Appl. No.: 10/746,360

(22) Filed: Dec. 29, 2003

(51) Int. Cl.[7] ..... A01H 5/00
(52) U.S. Cl. ..... Plt./226
(58) Field of Search ..... Plt./226

*Primary Examiner*—Kent Bell

(57) ABSTRACT

A new cultivar of *Brugmansia* plant named 'Miner's Claim' that is characterized by upright, spreading habit, variegated cream-white and light green foliage, and large salmon-pink flowers. In combination these traits set 'Miner's Claim' apart from all other existing varieties of *Brugmansia* known to the inventor.

2 Drawing Sheets

Genus, species: *Brugmansia×hybrida*.
Varietal denomination: 'Miner's Claim'.

BACKGROUND OF THE INVENTION

The present invention relates to a new and distinct cultivar of angels trumpet grown for use as an ornamental shrub. The new cultivar is known botanically as *Brugmansia×hybrida* and will be referred to hereinafter by the cultivar name 'Miner's Claim'.

'Miner's Claim' was discovered as a naturally occurring branch sport in a cultivated area of Monterey, Calif. in 1999. The sport was found on one individual plant within a block of commercially produced *Brugmansia* 'Frosty Pink', and selected by the inventor for low vigor, and broadly conspicuous variegation of foliage. The parent plant is *Brugmansia* 'Frosty Pink' (unpatented). The closest comparison plant is *Brugmansia* 'Frosty Pink'. 'Miner's Claim' is distinguishable from 'Frosty Pink' by conspicuous cream-white and light green marginal variegation of the foliage.

'Miner's Claim' is evergreen and suitable for use as an ornamental shrub. 'Miner's Claim' exhibits an upright, spreading habit, variegated foliage and strongly fragrant, salmon-pink flowers. The distinguishing characteristics are slow growth and variegated foliage. The cultural requirements are rich, highly amended soil and direct sunlight during half the daylight hours. When planted in complete bright shade 'Miner's Claim' will grow slower than its typically slow growth rate.

The first asexual reproduction of 'Miner's Claim' was conducted under the direct supervision of the inventor in a cultivated area of Monterey, Calif. in 2000. The method used for asexual propagation was softwood cuttings. The characteristics of the new cultivar have been determined stable and are reproduced true to type in successive generations.

SUMMARY OF THE INVENTION

The following traits have been repeatedly observed and represent the characteristics of the new *Brugmansia* cultivar 'Miner's Claim'. These traits in combination distinguish 'Miner's Claim' from all other commercial varieties of *Brugmansia* known to the inventor. 'Miner's Claim' has not been tested under all possible conditions and phenotypic differences may be observed with variations in environmental, climatic and cultural conditions, without however, any difference in genotype.

1. *Brugmansia* 'Miner's Claim' exhibits an upright, spreading habit.
2. *Brugmansia* 'Miner's Claim' is slow-growing, exhibiting fifty-percent the vigor of its parent.
3. *Brugmansia* 'Miner's Claim' exhibits cream-white and light green marginal variegation of the foliage.
4. *Brugmansia* 'Miner's Claim' exhibits large semi-pendulous trumpet-shaped salmon-pink flowers.
5. *Brugmansia* 'Miner's Claim' is 3.4 meters. in width and 3.2 meters. in height at maturity.
6. *Brugmansia* 'Miner's Claim' is propagated by the method of softwood cuttings.
7. *Brugmansia* 'Miner's Claim' is suitable for use as an ornamental shrub.
8. With protection *Brugmansia* 'Miner's Claim' is hardy to USDA Zone 9a.

BRIEF DESCRIPTION OF THE DRAWINGS

The accompanying color drawings illustrate the overall appearance of the new variety 'Miner's Claim' showing the colors as true as it is reasonably possible to obtain in colored reproductions of this type. Colors in the drawings may differ from the color values cited in the detailed botanical description, which accurately describe the actual colors of the new variety 'Miner's Claim'. The plants in the drawings were grown in 5-liter containers and treated with MARATHON® insecticide.

The first drawing illustrates the entire plant, before bloom, from a side perspective.

The second drawing is a close-up view of the flower and foliage.

The drawings were made using conventional techniques and although colors may appear different from actual colors due to light reflectance they are as accurate as possible by conventional photography.

BOTANICAL DESCRIPTION OF THE PLANT

The following is a detailed description of 'Miner's Claim' as grown In Monterey, Calif. Data was collected from 5-liter container plants during their first season of growth, that is from 6 months to 9 months (in flower) from a cutting. The color determinations are in accordance with the 2001 Edition of the Colour Chart of The Royal Horticultural Society, London, England, except where general color terms of ordinary dictionary significance are used. Growing conditions, diseases and pests are similar to that of other *Brugmansia*. There are no growing problems known to the inventor.

Botanical classification: *Brugmansia* 'Miner's Claim'.
Species: ×*hybrida*.
Commercial classification: Perennial shrub.
Use: Ornamental.
Cultural requirements: Performs best when given regular water, rich highly amended soil, and planted where it will receive direct sunlight for half of daylight hours. When planted in bright shade it will grow with less than the typical slow vigor.
Parentage: *Brugmansia* 'Miner's Claim' originated as a branch sport on one individual plant within a block of commercially grown *Brugmansia* 'Frosty Pink'.
*Parent plant.*—*Brugmansia* 'Frosty Pink'.
Plant description:
*Seasonal interest.*—Blooms spring, summer and fall. Variegated foliage year-round.
*Plant habit.*—Upright and spreading (to eventually form canopy).
*Plant shape* (*at maturity*).—Produces rounded canopy.
*Vigor.*—Moderate to low vigor in comparison to parent plant.
*Sexuality.*—Bisexual.
*Height* (*at maturity*).—3.2 meters in height at maturity.
*Width* (*at maturity*).—3.4 meters in width at maturity.
*Pollination requirements.*—None.
*Hardiness.*—Hardy to USDA Zone 9a. Will suffer frost damage below 0° Centigrade.
*Root system.*—Robust fibrous roots.
*Propagation.*—Propagation is accomplished using softwood cuttings. Robust fibrous roots develop quickly, preferably from non-flowering branches.
*Time and temperature to develop roots.*—1–2 weeks are needed at 21–24° Centigrade for an initial cutting to develop roots.
*Crop time.*—4–5 months are needed to produce a finished 1-liter container from a rooted cutting.
*Plant dimensions* (*at maturity*).—3.2 meters. in height and 3.4 meters in width at maturity.
*Susceptibility to disease and pest.*—Susceptible to whitefly, aphids and mites.
*Seasonal interest.*—Flowers spring through fall, and sporadically in summer.
*Special considerations.*—All parts of plant are poisonous.
Stem:
*Stem shape.*—Cylindrical.
*Stem dimensions.*—180 cm. in length and 1–6 cm. in diameter.
*Stem color.*—Individual colors 145D and 146C are present on an individual stem.
*Branching arrangement.*—Alternate.
*Internode length.*—1.5 cm. to 3 cm. between nodes.
*Node color.*—146C.
*Node dimensions.*—3 mm. in diameter and 7 mm. in height.
Foliage:
*Type.*—Evergreen.
*Arrangement.*—Leaves are alternate.
*Shape.*—Lanceolate.
*Division.*—Simple.
*Apex.*—Acute to mucronate.
*Base.*—Attenuate to finely oblique.
*Venation pattern.*—Pinnate.
*Vein color* (*abaxial surface*).—145D.
*Vein color* (*adaxial surface*).—147C.
*Mature leaf dimensions.*—34 cm. in length and 12 cm. in width.
*Leaf margins* (*young and mature*).—Entire and shallowly undulate on basal end.
*Attachment.*—Petiolate.
*Petiole dimensions.*—7.5 cm. in length and 60 mm. in width.
*Petiole surface.*—Finely pubescent.
*Petiole color.*—A combination of 145A and 145B.
*Stipules.*—Absent.
*Leaf surfaces* (*adaxial and abaxial*).—Coarsely glabrous with only a few fine hairs.
*Youngest leaf color* (*adaxial and abaxial surfaces*).—Colors 146A, 146B, and 151A are individually present on individual leaf.
*Partially grown leaf color* (*adaxial and abaxial surfaces*).—Colors 147A, 146C, and 160A are individually present on individual leaf.
*Mature leaf color* (*adaxial and abaxial surfaces*).—Colors 147A, 148B and 160C are individually present on individual leaf.
*Leaf fragrance.*—Herbaceous and slightly rank.
Flowers:
*Inflorescence type.*—Solitary.
*Shape.*—Funnelform to campanulate.
*Aspect.*—Semi-pendulous.
*Blooming seasons.*—Heaviest blooming is spring through fall.
*Quantity of flowers per branch.*—5–10 flowers per individual flowering branch.
*Flower dimensions.*—Approximately 15 cm. in diameter at widest part and from 25 cm to 35 cm in length (including calyx, corolla and petals).
*Persistent or self-cleaning.*—Self-cleaning.
*Bud dimensions.*—8.6 cm. in length and 1.8 cm. in width.
*Bud shape.*—Narrowly oblong.
*Bud color.*—144A.
*Corolla tube depth.*—From 20 cm to 30 cm when measured to base of the petal lobes.
*Petals.*—Five in number.
*Petal surfaces* (*adaxial and abaxial*).—Glabrous.
*Petal shape.*—Closest to spatulate, three convex folds or ridges, each petal lobed.
*Fused or unfused.*—Fused petals.
*Petal dimensions.*—Length: From 25 cm to 35 cm measured along the ridge. Width: From 6 cm to 8 cm at the base of each lobe.
*Lobes.*—Approximately 8 cm in length (base to apex) and 6 cm–8 cm in width.
*Apex.*—Reflexed, acuminate with extended point approximately 0.5 cm to 1 cm long and 2 mm wide.
*Newly emerging petal color* (*adaxial and abaxial surfaces*).—Individual flowers range in color from the combined colors 144A–144B to the combined colors 151A–151B.

*Petal color* (*adaxial and abaxial surfaces*).—35C.

*Petal ridges* (*adaxial surface*).—Pale green becoming lighter (cream) towards apex.

*Petal margin.*—Broadly sinuous.

*Calyx color.*—144A.

*Calyx shape.*—Tubular.

*Calyx dimensions.*—8.3 cm. in length and 2.2 cm. in width.

*Calyx surface.*—Sparsely pubescent.

*Sepals.*—Five in number.

*Sepal margin.*—Entire.

*Sepal apex.*—Acute.

*Peduncle dimensions.*—5 cm. in length and 6 mm in width.

*Peduncle surface.*—Minutely pubescent.

*Peduncle color.*—144B.

*Peduncle shape.*—Cylindrical.

*Flower fragrance.*—Strongly sweet and slightly musky nocturnal scent.

Reproductive organs:

*Stamens.*—Five in number.

*Stamen color.*—155C.

*Stamen dimensions.*—The width of the stamens is 1.5 mm. and the length is 15.7 cm. (including anther).

*Anther color.*—156A.

*Anther dimensions.*—2 mm. in width and 2.7 cm. in length.

*Anther attachment.*—Basafixed.

*Anther shape.*—Introrse with longitudinal slits fused with other stamens at margins to form a ring through which the style exserts.

*Pollen color.*—156A.

*Amount of pollen.*—Moderate amount.

*Pistil.*—One.

*Pistil shape.*—Slender filament.

*Pistil dimensions.*—17.75 cm. in length (from ovary apex) and 1.5 mm. in width.

*Pistil color.*—155C.

*Style shape.*—Slender filament.

*Style color.*—155C.

*Stigma shape.*—A combination of fused clavate, fused trifid and fused bifid individually present on individual plant.

*Stigma color.*—Colors of stigmas range from 161B to 161C in individual flowers of an individual plant.

*Stigma dimensions.*—3 mm. in diameter and 12 mm. in length.

*Ovary position.*—Superior.

*Ovary color.*—144B.

*Ovary shape.*—Oval.

*Ovary dimensions.*—16–20 mm. in height and 4 mm. in diameter.

Seed production: No seed production has been observed to date.

It is claimed:

1. A new and distinct cultivar of *Brugmansia* plant named 'Miner's Claim' as described and illustrated herein.

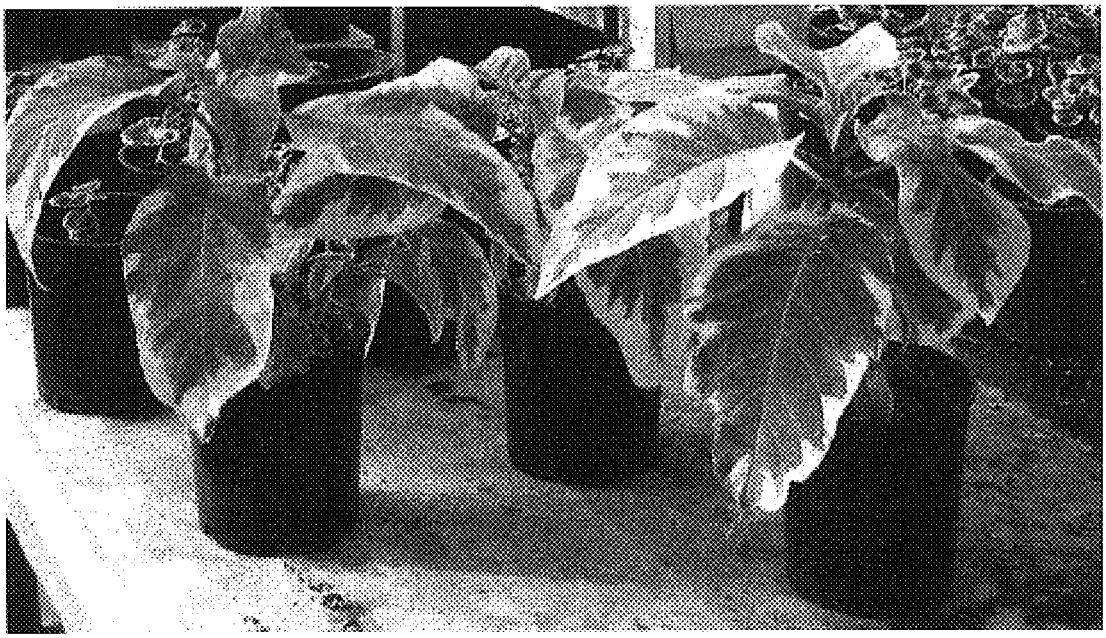

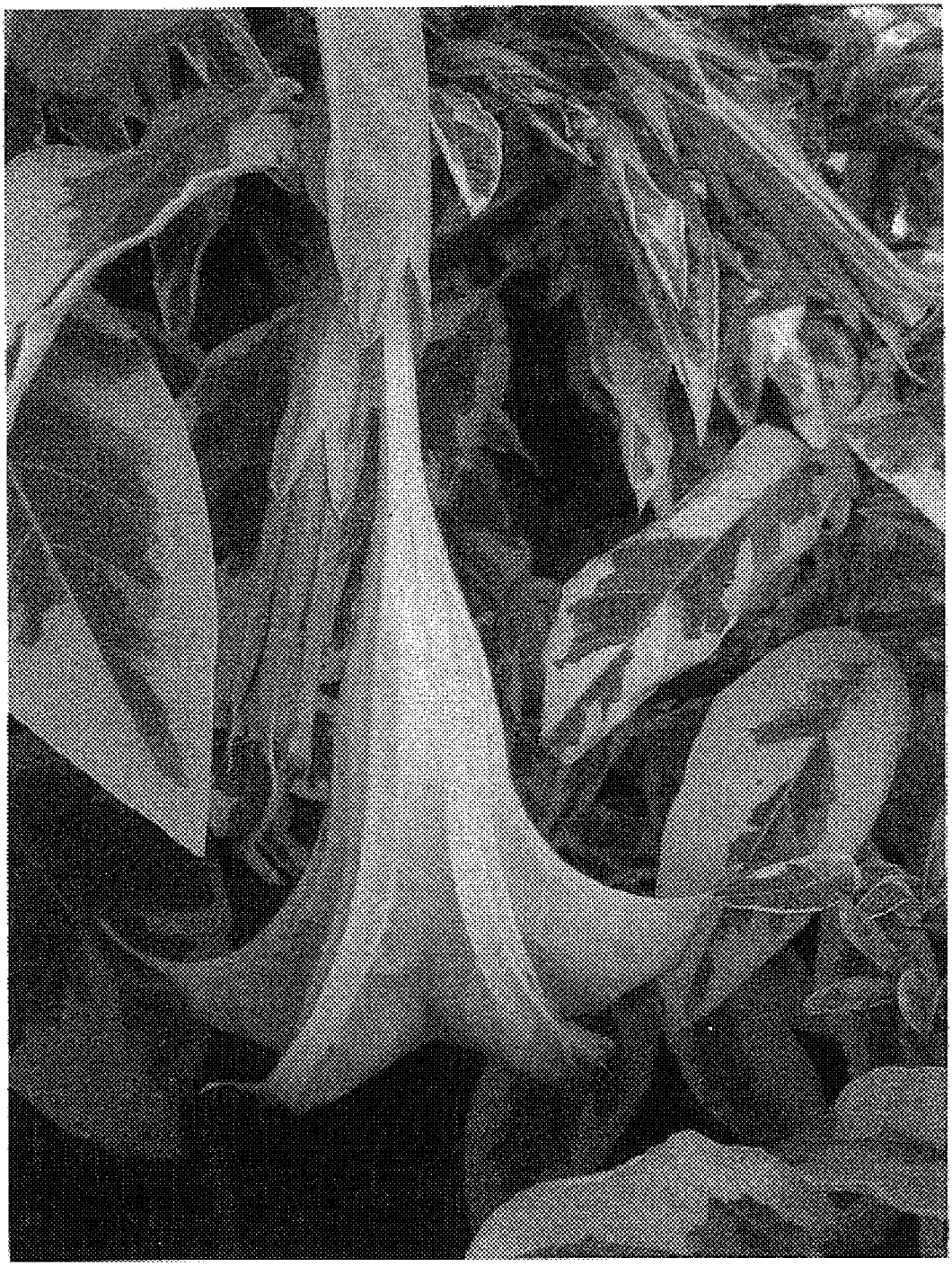

* * * * *